United States Patent [19]
Luceri

[11] Patent Number: 5,807,365
[45] Date of Patent: Sep. 15, 1998

[54] GARMENT SHIELD

[75] Inventor: Thomas Luceri, Bridgewater, N.J.

[73] Assignee: McNeil-PPC, Inc., Skillman, N.J.

[21] Appl. No.: 852,306

[22] Filed: May 7, 1997

Related U.S. Application Data

[60] Continuation of Ser. No. 425,963, Jun. 5, 1995, abandoned, which is a division of Ser. No. 389,431, Feb. 14, 1995, abandoned, which is a continuation of Ser. No. 960,664, Oct. 14, 1992, abandoned.

[51] Int. Cl.$^6$ .............................. A61F 13/15; A61F 13/20
[52] U.S. Cl. .................. 604/367; 604/358; 604/365; 604/366; 604/370; 604/372; 604/375; 604/378; 604/379; 604/380; 604/385.1; 604/393
[58] Field of Search ...................... 604/358, 365, 604/366, 367, 370, 372, 385.1, 375, 378–380, 393, 386, 387, 383, 389, 390; 156/66, 230, 234, 238, 240, 540; 602/54–58, 903

[56] References Cited

U.S. PATENT DOCUMENTS

| | | | |
|---|---|---|---|
| 4,154,883 | 5/1979 | Elias | 428/171 |
| 4,622,089 | 11/1986 | Lauritzen | 156/250 |
| 4,650,481 | 3/1987 | O'Connor et al. | 604/380 |
| 4,731,066 | 3/1988 | Korpman | 604/366 |
| 4,883,707 | 11/1989 | Newkirk | 604/370 |
| 4,886,697 | 12/1989 | Perdelwitz, et al. | 428/192 |
| 5,334,177 | 8/1994 | Cohen | 604/378 |

*Primary Examiner*—Mickey Yu
*Assistant Examiner*—Francis K. Cuddihy

[57] ABSTRACT

A disposable panty shield comprising a thin, highly absorbent pad having a body-contacting surface, an absorbent layer, a liquid barrier, a positioning means for attaching the pad to an undergarment, and a release layer to protect the positioning means prior to use wherein the has been densified by fusing all pad layers together in a manner such that the interstitial space between the individual fibers in the densified areas is not sufficient to readily allow fluid to flow through. Further, the densified areas are made contiguous such that fluid, when introduced or deposited on the pad, will be prevented or hindered from flowing to the edges of the pad.

16 Claims, 8 Drawing Sheets

GARMENT SHIELD

This is a continuation of application Ser. No. 08/425,963, filed Jun. 5, 1995, which is a division of application Ser. No. 08/389,431 filed on Feb. 14, 1995, which is a continuation application of Ser. No. 07/960,664 filed on Oct. 14, 1992, now abandoned, which are hereby incorporated by reference.

BACKGROUND OF THE INVENTION

The present invention relates to an absorbent article particularly suited for everyday feminine hygiene and for protecting an undergarment against staining from light, daily secretions and discharges. It comprises a very thin, lightweight, highly absorbent pad which is soft, supple and easily conformable to the body and the garment to which it is adhesively attached.

The prior art is replete with patents relating to protective pads and shields since the protection of undergarments from staining, especially for the many women who are troubled with frequent, light bodily discharges, has been a long standing problem. These patents generally describe layered structures having a porous body contacting layer overlying, a liquid impermeable garment side barrier layer, and a layer of absorbent material between the body contacting layer and the barrier layer. An adhesive is attached to the garment side of the fluid barrier to secure the assembled shield to the crotch portion of an undergarment. And, a release layer is removably affixed to the adhesive layer to keep the adhesive from making contact to anything until it is placed in the undergarment.

While such prior art pads undoubtedly function to protect the undergarments to which they are applied, they are deficient in one primary area of performance. They tend to draw fluid toward the lateral and longitudinal edges of the pad, increasing the likelihood of failure by allowing leakage off the pad onto the wearer's clothes.

Some body-contacting layers of the prior art which are absorbent, porous, dry-laid, nonwoven webs or scrim type materials such as those described by I. S. Ness in U.S. Pat. No. 4,880,419 and by Campau in U.S. Pat. No. 3,044,467, Hendricks in U.S. Pat. No. 3,463,154 and Sneider in U.S. Pat. No. 3,570,491. Such materials are often coarse textured and harsh to the touch and, because of their absorbency, wet from the top surface down during use resulting in a constantly moist surface against the skin.

There are also some body-contacting layers of the prior art such as those described by T. J. Luceri in U.S. Pat. No. 4,795,455, by S. Cadieux in E.P. Pat. No. 359,501, by A. T. Mays in E.P. U.S. Pat. No. 70,163, and by R. P. James in U.S. Pat. No. 4,368,323 which are nonwovens made from hydrophobic fibers which have been coated with an adhesive or have been subjected to heat and/or pressure to fuse the individual fibers to each other. Such materials tend to have only limited absorption but serve to allow passage to lower layers for absorption and retention. As a result, the fluid is wicked away from the body, leaving the surface of the body-contacting layer feeling dryer to the touch.

The use of hydrophobic fibers for the body contacting layer allows fluid to pass through to the absorbent layer beneath yet will not retain moisture on the surface layer, thus providing greater comfort to the wearer by feeling dry for a longer period of time. The desirability of such a feature has been recognized by Levesque U.S. Pat. No. 3,838,692 who describes a chemical method of providing porosity to hydrophobic materials.

The absorbent layers taught by the prior art usually consists of pulp fluff as described by S. L. Kopolow in U.S. Pat. No. 4,552,618 and 4,555,192, by D. C. Holtman in U.S. Pat. No. 4,544,596 and 4,536,432, by P. K. Chatterjee in U.S. Pat. No. 4,474,949.

Alternatively, the absorbent layer of the prior art may consist of blends of pulp fluff and synthetic fibers as described by Malaney in U.S. Pat. Nos. 4,756,786 and in 4,684,570. Or, the absorbent layer may be thermoplastic fibers co-formed with pulp fibers.

It is also possible to disperse into the absorbent layer a super absorbent polymer such as those taught by S. Dabi in U.S. Pat. No. 4,494,963, by I. S. Ness in U.S. Pat. No. 4,880,419 and by J. Roller in U.S. Pat. No. 4,443,492.

The liquid impermeable barrier layer, located between the absorbent layer and the garment, is commonly made of polyethylene, polypropylene, or a like material. Such layers are taught in U.S. Pat. No. 4,731,066 by R. Korpman.

Generally, the earlier prior art teaches absorbent pads made of wood pulp fluff that, when properly manufactured to absorb large quantities of fluid, are thick and bulky. Recent developments in the art teach the use of materials such as sphagnum peat moss (such as that taught by Y. Levesque in U.S. Pat. No. 4,507,122) and super absorbent polymers which, pound for pound, absorb much greater quantities of fluid than pulp allowing for the manufacture of much thinner absorbent pads.

The prior art also teaches the application of heat and/or pressure to bind the fibers of the absorbent layer together into densified areas. As fluid makes contact with such densified areas, the fluid tends to wick across the layer, away from the point of fluid introduction. This action helps to inhibit local saturation of the pad which is one cause of pad failure. See, for example, U.S. Pat. No. 4,059,114 to Richards and U.S. Pat. No. 4,886,697 to Perdelwitz et al.

Once fluid has been introduced to the body contacting surface, pad construction is designed to cause the fluid to flow into the absorbent layer and remain there until disposal of the pad. However, the garment side of the structure is usually made with a liquid impermeable barrier layer which, in the event fluid continues to flow through the pad to the garment side, prevents leakage onto the wearer's garments.

Viewing this prior art, however, it is readily apparent that little thought has been given toward keeping the fluid from migrating to the lateral and longitudinal edges of the absorbent pad. While transverse wicking takes place, the design of the densified areas is such that the fluid is not prevented, in fact it may be encouraged, to flow away from the point of fluid introduction in the center of the pad to the edges of the pad increasing the chances of failure. While perimeter barriers have been taught by the prior art, there exists a need to wick fluid from the point of introduction on the pad yet still keep it compartmentalized so that it is prohibited, or at least hindered, from flowing toward the edge of the pad. The present invention meets this and other objectives which will become apparent.

SUMMARY OF THE INVENTION

The disposable shield of the present invention comprises a thin, highly absorbent pad having a body-contacting surface, an absorbent layer, a liquid barrier, a positioning means for attaching the pad to an undergarment, and a release layer to protect the positioning means prior to use. The pad further comprises densified areas which have been made by fusing all pad layers together in a manner such that the interstitial space between the individual fibers in the densified areas is insufficient to readily allow fluid to flow through. The densified areas are made contiguous such that fluid, when introduced or deposited on the pad, will be prevented or hindered from flowing to the edges of the pad.

The present invention also involves a method of manufacturing the absorbent pad by applying heat and pressure to fuse all three layers of the pad—the body contacting layer, the absorbent layer, and the garment side layer—together to form fluid barriers in patterns which cause fluid to be compartmentalized on the pad, preventing or hindering its flow toward the pad edges.

BRIEF DESCRIPTION OF THE DRAWINGS

In the accompanying diagrammatic drawings which illustrate the invention:

FIG. 7 is a photograph showing side-by-side comparison of open ended embossing lines versus a closed inner barrier.

DETAILED DESCRIPTION OF THE INVENTION

Figure 1:
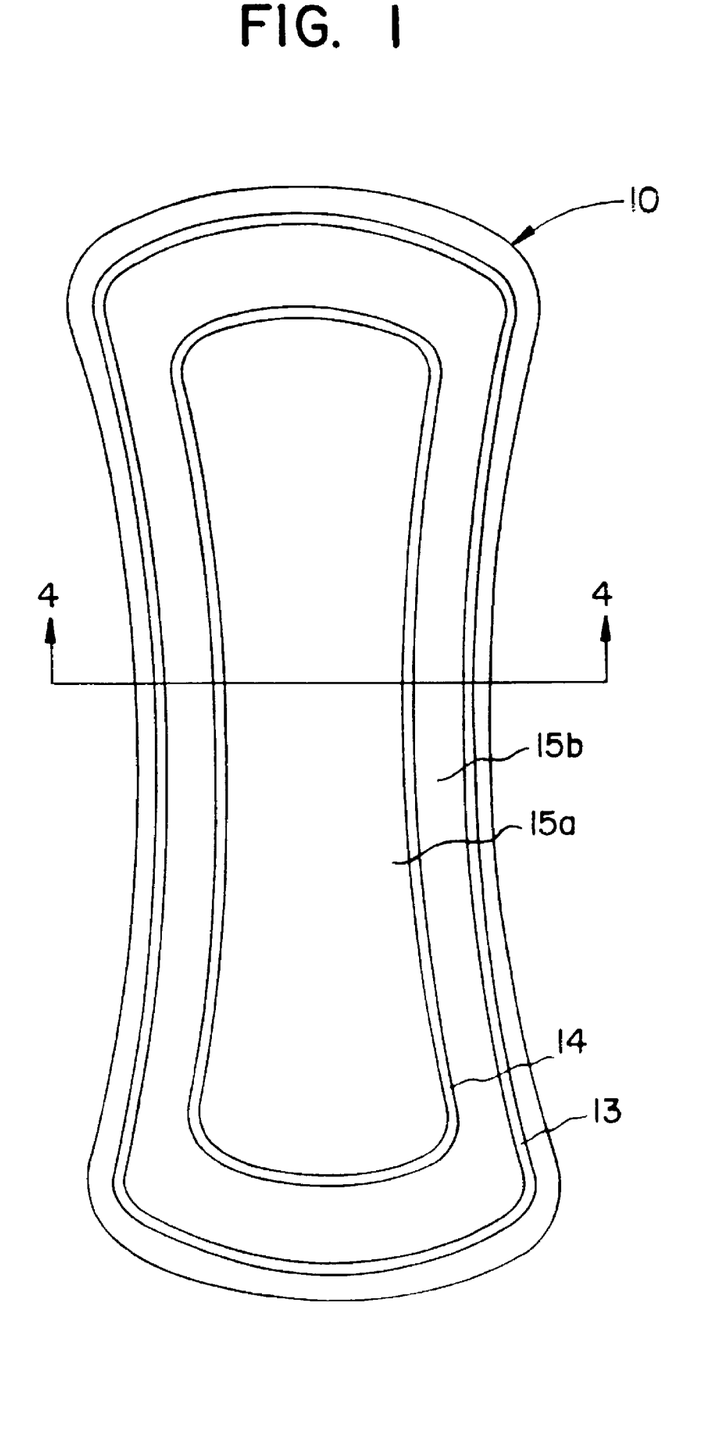
FIG. 1 is a plan view of one embodiment of a shield of the present invention.
Figure 2:
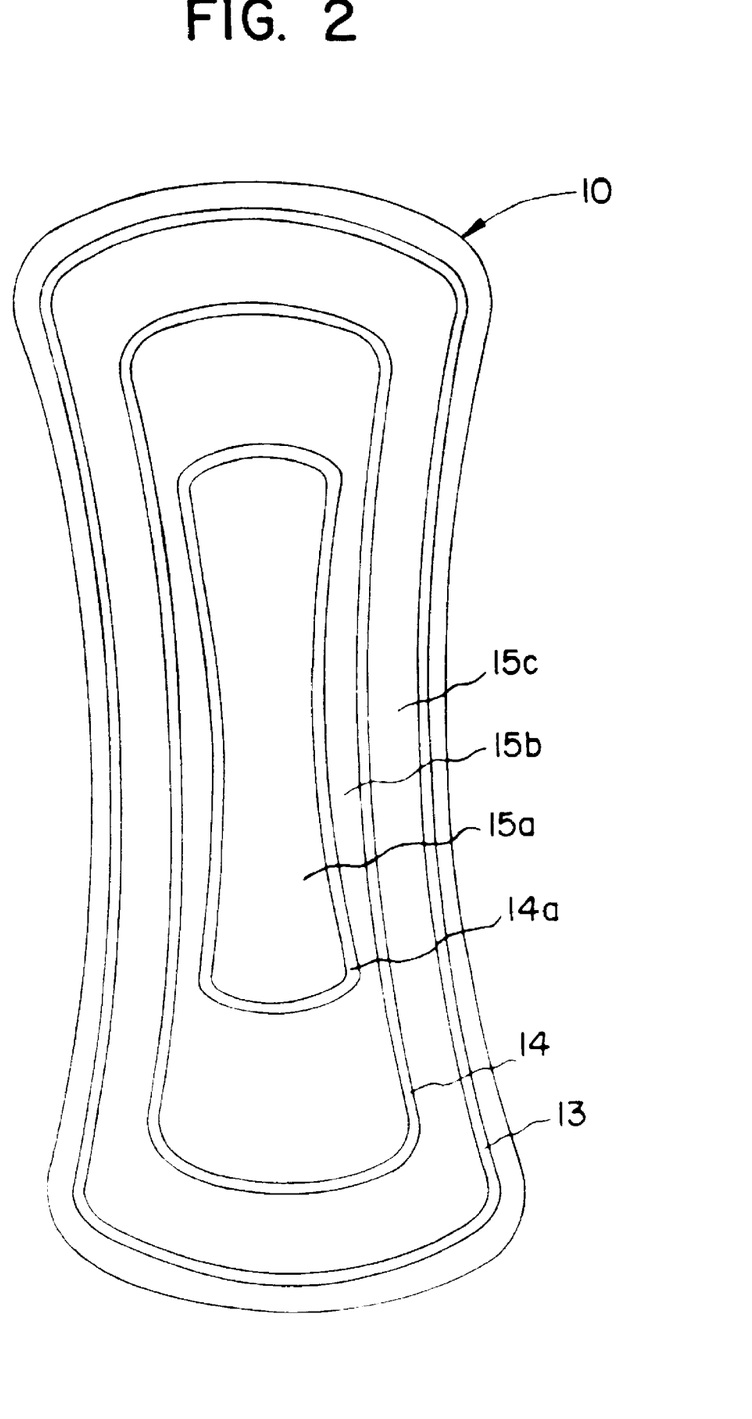
FIG. 2 and 3 are plan views of two modified shield shapes.
Figure 3:
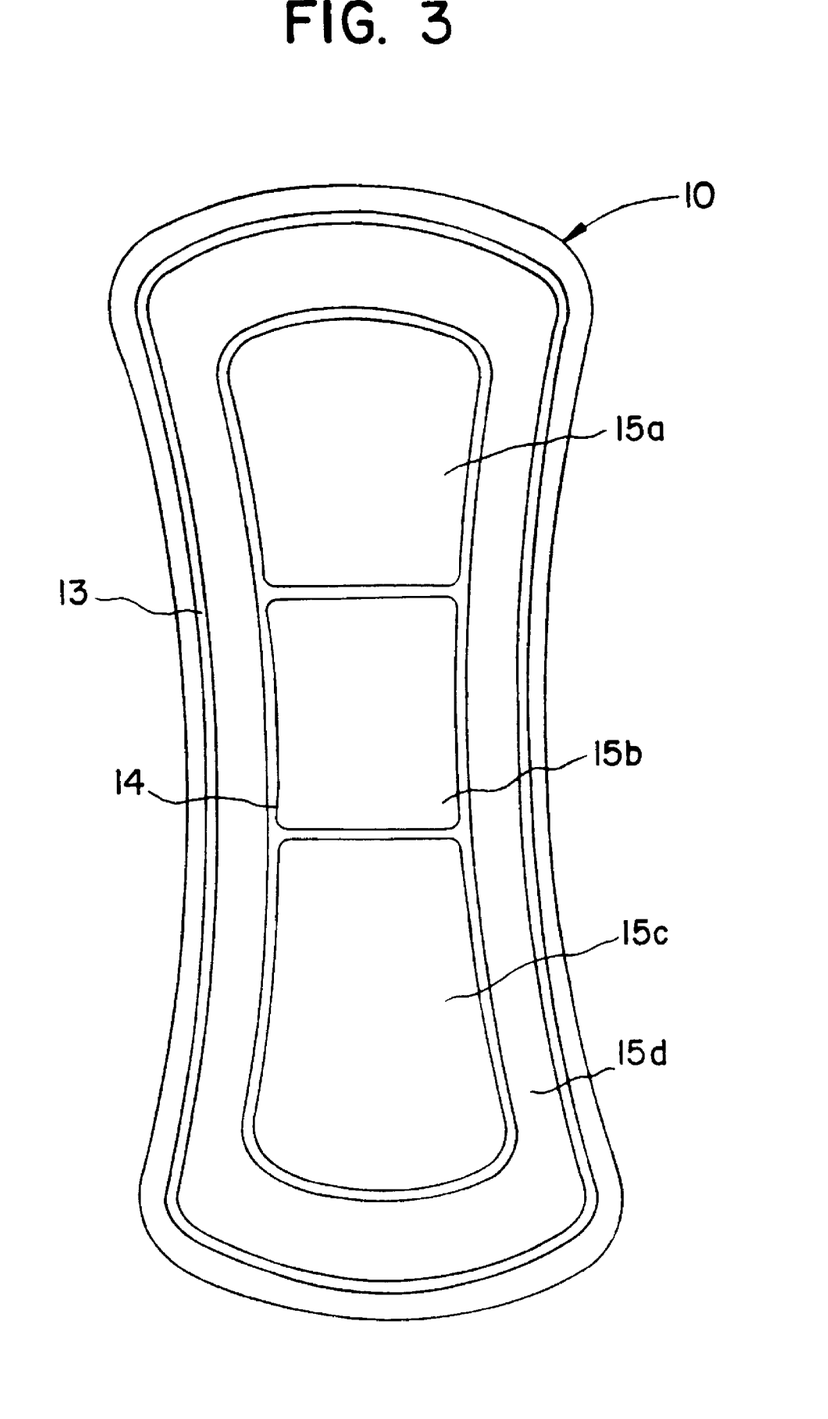

Referring now more particularly to the drawings, FIG. 1 shows a pad 10 of the present invention in plan view. The pad there shown has an outer fluid barrier 13 near the perimeter of the pad and an inner fluid barrier 14 inwardly spaced from the outer fluid barrier 13. These fluid barriers serve to separate, or compartmentalize, the pad into distinct absorbing areas 15a and 15b. Other pads are shown in FIGS. 2 and 3 having variation in the design of the fluid barriers and the absorbing areas. Many others designs will suggest themselves.

The pad 10 is constructed with an cover layer 11 having a body-contacting surface 12. In one embodiment, cover layer 11 comprises a nonwoven fibrous web formed of staple hydrophobic textile fibers. Such fibers may be unified by being coated with a watery-insoluble rubbery fiber-binding resin so that all of the individual fibers are substantially covered with a resin coat, thus bonding them together at their crossing points while leaving the interstices of the web unfilled.

The cover layer 11 can also be made from a porous, substantially planar flexible polymeric coating on the surface of a bonded staple hydrophobic fiber web or the outermost surface of a lofty web of blended fibers in an integral pad construction. Such a surface, due to the flatness of the polymeric coating, has an unusually soft, smooth feeling and is pleasing to the touch.

It is, however, preferable that the fibers of cover layer 11 be thermoplastic or, more preferable, a mixture of two or more types of thermoplastic fibers having different melting points. Upon application of heat and pressure sufficient to melt at least one of the fiber types, the remaining unmelted fibers will be thermobonded or fused together into a porous web. This processing step is described more fully in U.S. Pat. No. 4,622,089, Lauritzen, hereby incorporated by reference.

The fibrous materials found to be satisfactory in the making of cover layer 11 have been found to be blends of two thermoplastic fibers having distinguishable melting temperatures. Bicomponent fibers, fibers with an inner core of a thermoplastic fiber, e.g., polyester, surrounded by an outer sheath of thermoplastic, e.g., polyethylene, having a melting point much lower than the core, have been found to be the best fibers to work with from processing and performance standpoints. Such fibrous materials are taught by U.S. Pat. No. 4,622,089, Lauritzen. It is also conceivable that the materials for cover layer 11 may be coformed blends of pulp fluff and thermoplastic fibers, e.g., polypropylene, It has been found to be acceptable to use fibrous materials for cover layer 11 having a denier in the range of from about 1.0 to about 4.0. Superior performance, from the standpoint of comfort, is believed to result from a denier of from about 1.5 to about 3.5 or, most preferably, from a denier of about 1.5 to about 2.0. Currently, commercialization is about to begin with a denier of 1.8.

Fiber length for cover layer 11 has been found to be satisfactory if in the range of from about 0.5 inches to about 2.5 inches.

The resulting web is a thin, pliable, resilient, porous, cloth-like fabric whose top surface has a soft, smooth, pleasing, tactile quality. This web may be fed directly and continuously into the manufacturing process for the pad 10 of this invention. Or, it may be collected and stored for later use.

Figure 4:
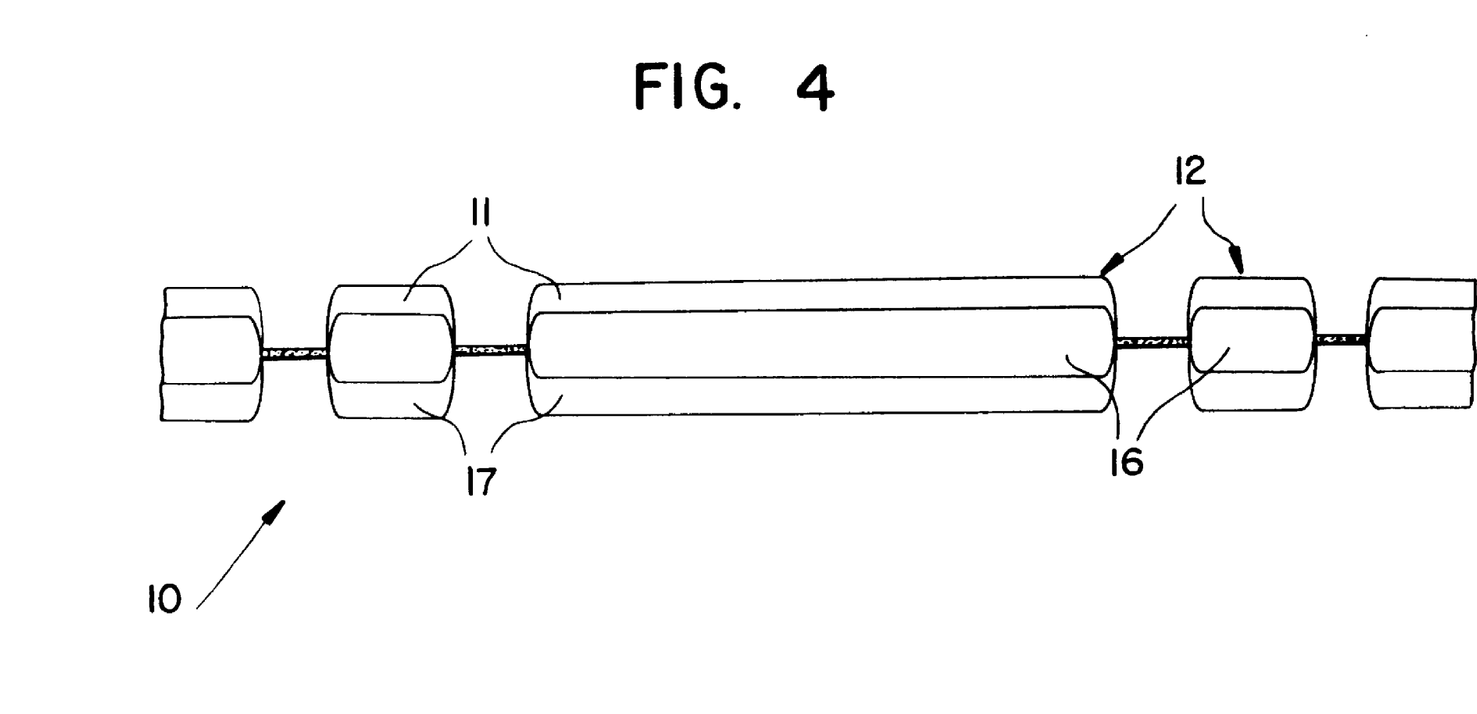
FIG. 4 is an enlarged section taken along line 4—4 of FIG. 1.
Figure 5:
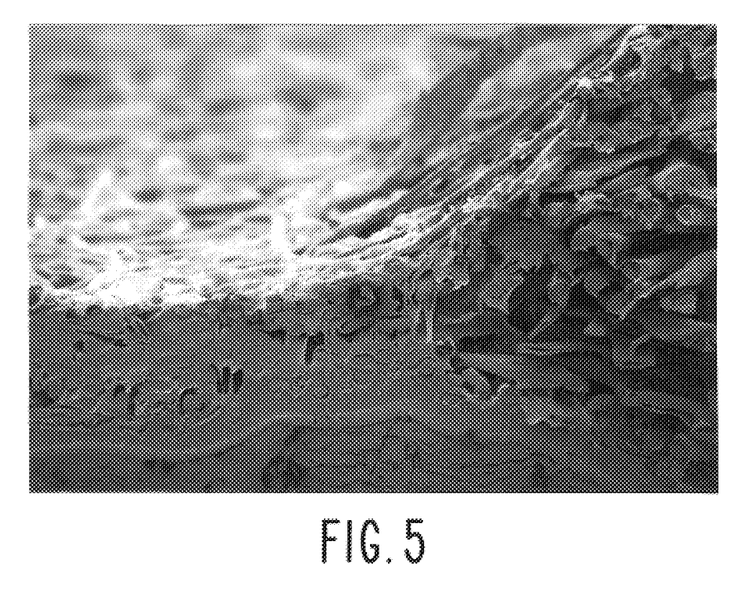
FIG. 5 is a photograph showing a greatly enlarged section of the fluid barriers.

Referring to FIG. 4, it can be seen that immediately below and in heat bonded relationship with cover layer 11 is an absorbent layer 16 comprising a blend of thermoplastic fibers. It is preferable that the thermoplastic fibers of absorbent layer 16 be a mixture of two or more types of thermoplastic fibers having different melting points. Bicomponent fibers, fibers with an inner core of a thermoplastic fiber, e.g., polyester, surrounded by an outer sheath of thermoplastic, e.g., polyethylene, having a melting point much lower than the core, have been found to be the best fibers to work with from processing and performance standpoints. Like cover layer 11 above it, upon application of heat and pressure sufficient to melt at least one of the fiber types, the remaining unmelted fibers will be thermobonded or fused together into a porous web.

It is also preferable to include cellulosic pulp fibers with the thermoplastic fibers in absorbent layer 16. Since thermoplastic fibers, without further treatment, are essentially hydrophobic, absorbent layer 16 will not effectively draw fluid away from cover layer 11 absent some hydrophilic material. It is important to have sufficient pulp to absorb fluid. However, as will be described more fully below, it is also important to have a sufficient amount of thermoplastic fibers so that, when the layer is heat bonded (as will be described more fully below) there will be sufficient melting of thermoplastic to fill the interstitial void space in the web. An acceptable amount of pulp for effective absorbency is from about 20% to about 95% by weight. Conversely, an acceptable amount of thermoplastic fibers is from about 5% to about 80% by weight. A preferred amount of pulp would be in the range of from about 20% to about 60% by weight (with thermoplastic fibers being in the range of from about 40% to about 80%). A more preferred amount of pulp would be in the range of from about 20% to about 40% by weight (with thermoplastic fibers being in the range of from about 60% to about 80%).

Another way to characterize the ratio of thermoplastic to pulp is to look at the total amount of pulp and thermoplastic fibers in both cover layer 11 and absorbent layer 16. Since they are to be in heat bonded relationship, and (as will be described more fully below) it is desirable for some of the thermoplastic fibers in each layer to melt and fuse with each other, it is preferable that, the cover layer 11 and absorbent layer 16 together include at least 35% by weight thermoplastic fibers. It is more preferable that there be at least 60% by weight thermoplastic fibers in both layers.

Upon formation of the absorbent layer 16, the material may be fed directly and continuously into the manufacturing process for the pad 10 of this invention or it may be collected and used later. Bonding between the cover layer 11 and the absorbent layer 16 is accomplished by placing the layers in contact with each other and subjecting them to pressure and heat. This causes further melting of the fibers of the cover layer 11 and absorbent layer 16 resulting in thermobonding of the layers to each other upon cooling. This process is described more fully below.

It will, of course, be appreciated that the absorptive portion of the shield may be the central portion of an integrally formed pad member having a porous, planar, flexible polymeric coating as its top surface. In other embodiments of the present invention, the absorptive portion of the shield can utilize a variety of water immobilizing materials, e.g., superabsorbing polymers or peat moss, to increase fluid capacity or minimize pad bulk. Such materials are taught by Y. Levesque in U.S. Pat. No. 4,507,122; S. Dabi in U.S. Pat. No. 4,494,963; by I. S. Ness in U.S. Pat. No. 4,880,419; by J. Roller in U.S. Pat. No. 4,443,492; hereby incorporated by reference.

The fibrous materials found to be satisfactory in the making of absorbent layer 16 are the same fibrous materials used for cover layer 11. Bicomponent polyester/polyethylene fibers have been found to be the best fibers to work with from processing and performance standpoints. Although it has been found that using fibers having a denier of about 1.8 in cover layer 11 results in improved comfort, it is not necessary to use fibers of this denier for absorbent layer 16. Although any denier in the range of from about 1.0 to about 4.0 will suffice, from a cost standpoint a denier of from about 2.5 to about 3.5 or more preferably, a denier of about 3.0 will yield good performance with acceptable manufacturing costs.

Fiber length for absorbent layer 16 has been found to be satisfactory if in the range of from about 0.5 inches to about 2.5 inches.

It is clear that the major distinctions between cover layer 11 and absorbent layer 16 is the presence of pulp in absorbent layer 16 and the possibility of finer denier fibers in cover layer 11. However, since the ranges for denier for each layer overlap, it is possible and acceptable to use the same denier fibers for both the cover layer 11 and absorbent layer 16. In such a case, there is no real need for two separate and distinct layers. Instead, it is possible to construct the pad using one layer that has a body contacting surface and a surface which faces barrier layer 17 (which is described in more detail below). In such a case, however, it is important to remember that the body contacting surface should be devoid of pulp. One of the main functions of the body contacting surface is to provide an essentially hydrophobic surface so that fluid will not remain at the surface but will instead be drawn to the absorbent material below. Therefore, when constructing a pad having one layer (instead of the two heretofore taught) the web should be laid with 100% thermoplastic fibers for at least the first mil. Thereafter, the mixtures of pulp and thermoplastic fibers taught above should be used.

Immediately beneath and in heat bonded relationship with absorbent layer 16 is a barrier layer 17 in the form of a soft, pliable, fluid impermeable layer. Such layers can be either vapor permeable or vapor impermeable and are well known in the art. Such barriers are commonly a mixture of two thermoplastic materials such as polyethylene and low melt EVA. U.S. Pat. No. 4,731,066 by R. Korpman adequately teaches such barrier layers and is hereby incorporated by reference.

Typically, the barrier layer 17 is purchased and fed from rolls into the manufacturing process for pad 10. The barrier layer 17 is brought into contact with the surface of absorbent layer 16 opposite the cover layer 11. Bonding between the barrier layer 17 and the absorbent layer 16 is accomplished by subjecting them to pressure and heat. This causes further melting of the fibers of the absorbent layer 16 resulting in thermobonding of the layers to each other upon cooling. This bonding step, described more fully below, may be done at the same time as the bonding step between cover layer 11 and absorbent layer 16.

Improved contact between absorbent layer 16 and barrier 17 would result if an adhesive coating were applied to either layer before they were put together. These adhesives are not necessary at the areas where pressure and heat is applied to bond the layers together. However, in those areas where bonding does not take place, adhesives will improve the contact between the layers. Such adhesives are well known in the art. An example would be U.S. Pat. No. 4,526,577, hereby incorporated by reference.

Applying adhesive to at least 20 percent of the surface area between absorbent layer 16 and barrier layer 17 will result in adequate bonding. Preferably adhesive should be applied to at least 50 percent of the surface area. However, it should be noted that every incremental increase in adhesive coverage will either improve the contact, or at least make delayering less likely.

Positioner means 18, typically a pressure sensitive adhesive, is known in the art and is adequately taught in U.S. Pat. No. 4,554,191 by R. Korpman and in U.S. Pat. No. 4,335,026 by I. J. Balinth, hereby incorporated by reference. Positioner means 18 is a pressure sensitive adhesive that keeps the pad properly positioned on the wearer's underpants during use. It is attached to barrier layer 17 and, for packaging is covered with a release paper 19 that is easily removed just prior to use.

In order for the adhesive of positioner means 18 to function effectively under the conditions to which it is subjected and on the fabrics it will be contacting, not only is the selection of the adhesive itself important but also the intricate adhesive system must be balanced as to surface adhesion, compliancy, coating weight, backing adhesion and backing strength. To remove cleanly from the garment to which it is attached, the adhesive bond to the garment surface must be weaker than the cohesive strength of the adhesive per se, the bond strength of the adhesive to its backing material, and the intrinsic strength of the composite structure.

The positioner means preferably comprises a moisture vapor permeable adhesive which can be securely attached to fabrics normally made into undergarments and is capable of being easily removed therefrom without fabric damage or leaving noticeable adhesive residue thereon.

Disposal of the pad can be accomplished by rolling the body contacting surface to the inside and securing it with the adhesive backing.

Figure 6:
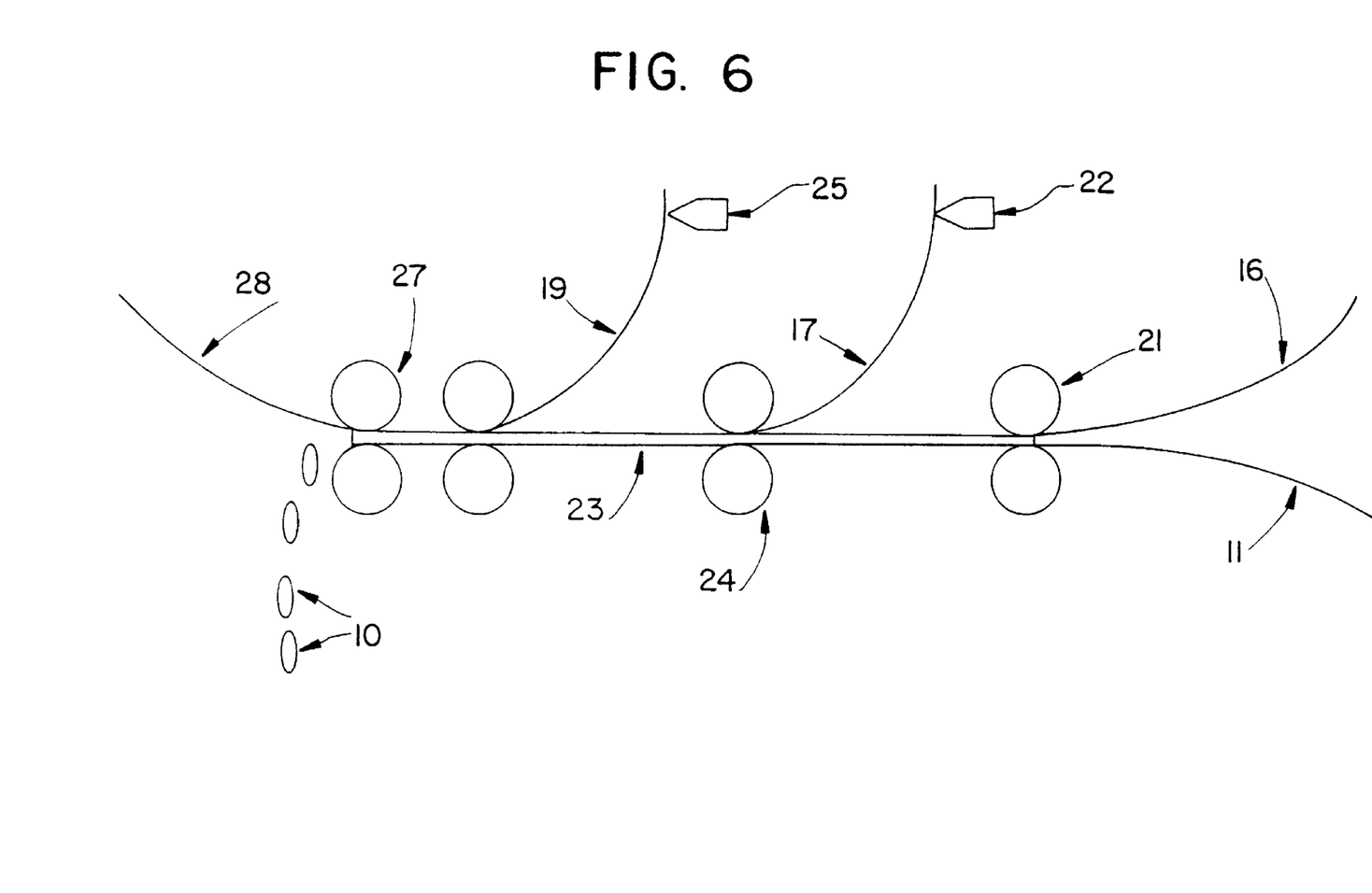
FIG. 6 is a schematic drawing of the manufacturing process of the present invention.

The component parts of the pad 10 are assembled according to the schematic diagram illustrated in FIG. 6 and unified by heat-sealing with a metal die platen configured with the desired shape of the pad and fluid barriers 13 and 14. Pad 10 is then trimmed to shape and size along the outer fluid barrier 13.

The process begins by placing cover layer 11 and absorbent layer 16 together. The two layers may, optionally, be fed into a pattern embosser 21 which prints a pattern onto the cover layer 11. The backing layer 17 is then fed to the cover layer/absorbent layer combination. For secure contact, an adhesive may be applied 22 just prior to applying the backing layer 17. If adhesive is applied it is preferred that the three layers be subjected to slight pressure to assure adequate contact between the backing layer 17 and the absorbent layer 16.

The pad material, shown in FIG. 6 as 23, is then fed into a sealing station 24 where pressure and heat are applied. The pressure and heat are controlled such that the temperature exceed the lower melting point of the thermoplastic materials in cover layer 11, absorbent layer 16, and barrier layer 17, but does not exceed the melting point of the remaining thermoplastic materials in each of the three layers.

It is important to note that, while higher temperatures and pressures are beneficial from the standpoint of fusing the layers together, if the temperature and/or pressure is too high pin holes will develop in the pad structure which will lead to failure. For instance, in the case producing 400–600 pads per minute, each pad comprised of polyester/polyethylene bicomponent fibers, it is important to keep the temperature the lower (pattern) roll of sealing station 24 within the range of from about 200° F. to about 400° F., preferably from about 250° F. to about 350° F.; and it is important to keep the temperature of the upper (anvil) roll within the range of from about 100° F. to about 200° F., preferably from about 125° F. to about 175° F. Further, it is important to keep the pressure within the range of from about 100 to about 600 psi, preferably within the range of from about 200 to about 500 psi.

Another related variable is the gap distance between the roll with the barrier seal mold and the anvil roll. As the gap distance decreases, fusing between the layers of the pad improves. However, at the same time the possibility of developing pin holes also increases. Therefore, in the case of polyester/polyethylene bicomponent fibers, it is important to keep the gap distance within the range of from about 0.01 to about 0.02 inches.

The outer barrier 13 and the inner barrier 14 formed from the application of pressure and heat are densified areas preferentially devoid of any interstitial pore space. As one of the thermoplastic fiber materials melts, the pressure forces it into the pore space, reducing the ability of the densified area to draw fluid into and through it by capillary action.

Positioning adhesive is then applied at 25 and release paper 19 is then applied at 26. The pad material is then fed into a cutting station 27, shown in FIG. 6 as a rotary operation. Thereafter, excess trim material is removed at 28 and the final pad 10 is sent for packaging.

It should be noted that pad 10 may be trimmed as close to outer fluid barrier 13 as possible without actually removing any of the fused material in the barrier. However, it is preferential to leave some portion of unfused material along the outer perimeter. This unfused material is less dense and softer than the fused barrier and is considerably softer to the touch.

Figure 8:
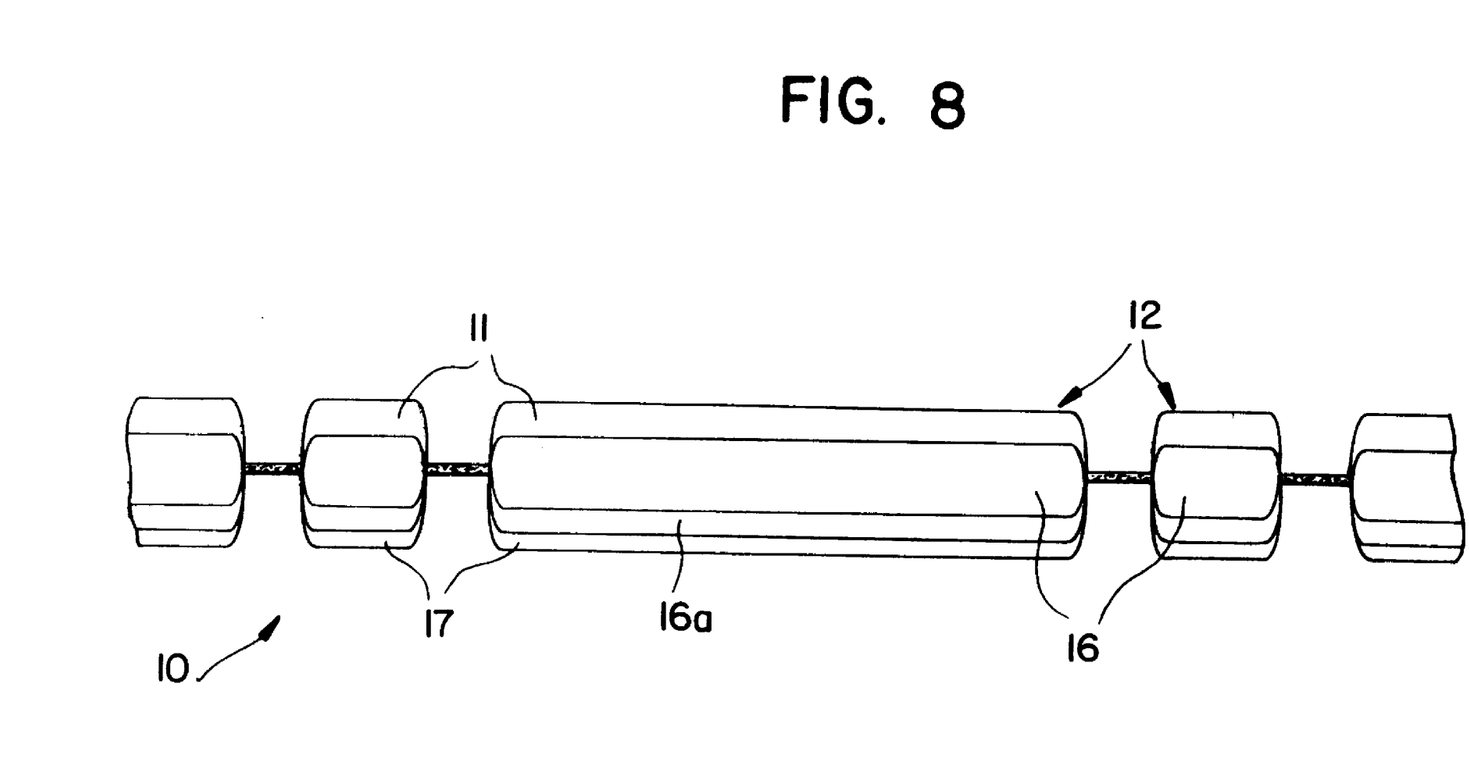
FIG. 8 is an enlarged cross-section of the pad of FIG. 4 that has been modified by the addition of a fibrous layer.

Referring to FIG. 8, an additional fibrous layer 16a may also be employed which is placed between absorbent layer 16 and backing layer 17. To understand the advantages of such an additional layer, it is first necessary to review the basic process.

As shown above and in FIG. 7, the normal manufacturing process for pads of this type involves first laying down a hydrophobic layer and applying heat to fuse the fibers into a web. An absorbent layer and a backing layer are then laid on top of the hydrophobic layer. In such a situation, the hydrophobic layer (intended to be the body-side layer) becomes needlessly compressed and stiff.

If a second hydrophobic layer, made from the same material as the first hydrophobic layer, is laid onto the absorbent layer, an advantageous result occurs. The second hydrophobic layer is not as compressed as the first hydrophobic layer and is softer to the touch. A backing layer can then be applied to the more compressed hydrophobic layer and the less compressed hydrophobic layer can become a softer, more pleasing body-side layer.

There is also an additional benefit. Pulp fluff is very dusty. By sandwiching the absorbent layer containing pulp between two fibrous thermoplastic layers, the dust in the operating environment is greatly reduced.

The manufacturing steps in this event are slightly different from those previously described in connection with FIG. 6. Firstly, fibrous layer 16a is laid onto absorbent layer 16 which is then laid onto layer 11. Then, backing layer 17 is applied to layer 16a. In such an arrangement, layer 11 then becomes the body-side, cover layer, layer 16a becomes merely a support layer between absorbent layer 16 and backing 17.

EXPERIMENTAL DATA

A comparison was made between the pad of the present invention (without layer 16a) and that of the closest prior art—U.S. Pat. No. 4,059,114, Richards.

Richards provides for longitudinally oriented line embossments that open at the longitudinal ends of the pad. Therefore, a side-by-side comparison was made to view the flow of fluid that was introduced in the pad of Richards and that of the present invention.

Two pads were prepared, shaped identically overall. In one, line embossments were placed which were open on the longitudinal ends. In the second, an inner barrier seal was placed which was closed. Two ml. of fluid was placed on each pad at a contact site half way between the center of the pad and one longitudinal end. After ten minutes a photograph, FIG. 7, was taken to illustrate how the fluid had dispersed in the pads.

In the pad with the open line embossments, it can be clearly seen that fluid has extended past the ends of the line embossments and is extending toward the longitudinal ends. Also, it can be clearly seen that fluid has flowed around the end of the rightmost embossment line to the perimeter seal. In the pad with the closed inner barrier, however, the fluid is clearly contained within the innermost seal with no pressure on the outer seal.

What is claimed is:

1. An absorbent pad having a perimeter and comprising a fibrous, body-side, cover layer; a fluid impermeable, garment-side backing layer; and a fibrous absorbent layer therebetween; wherein the cover layer, the absorbent layer, and the backing layer are each comprised of at least two thermoplastic materials having distinguishable melting points, and wherein the cover layer, the backing layer, and the absorbent layer are melted to each other to substantially fill the interfiber spaces thus forming a first fluid barrier proximate the perimeter and a contiguous second fluid barrier, spaced inwardly from the first fluid barrier to form separate, compartmentalized areas for absorbing liquids.

2. The absorbent pad of claim 1 wherein the at least two thermoplastic materials in the cover and absorbent layers comprise bicomponent fibers.

3. The absorbent pad of claim 1 which further comprises a layer positioned between the absorbent layer and the backing layer which additional layer is comprised of thermoplastic fibers.

4. The absorbent pad of claim 2 wherein the bicomponent fibers are comprised of a polyester core surrounded by a sheath of polyethylene.

5. The absorbent pad of claim 1 wherein the absorbent is further comprised of pulp fluff.

6. The absorbent pad of claim 5 wherein the pulp fluff is present in amounts ranging from about 20% to about 60% by weight and the at least two thermoplastic materials are present in amounts ranging from about 40% to about 80% by weight.

7. The absorbent pad of claim 5 wherein the pulp fluff is present in amounts ranging from about 20% to about 40% by weight and the at least two thermoplastic materials are present in amounts ranging from about 60% to about 80% by weight.

8. The absorbent pad of claim 1 wherein the cover layer has fibers with a denier from about 1.0 to about 4.0.

9. The absorbent pad of claim 8 wherein the absorbent layer has fibers with a denier from about 1.0 to about 4.0.

10. An absorbent pad comprising a fibrous, body-side, cover layer; a fluid impermeable, garment-side backing layer; and a fibrous absorbent layer therebetween; each of said layers comprising at least two thermoplastic materials having distinguishable melting points; wherein the cover layer, the backing layer, and the absorbent layer are melted to substantially fill the interfiber spaces thus forming a plurality of fluid barriers defining two or more compartmentalized areas for absorbing liquids; and wherein the cover layer and absorbent layer together comprise at least 60 wt-% thermoplastic fibers.

11. The absorbent pad of claim 10 wherein the at least two thermoplastic materials in the cover and absorbent layers comprise bicomponent fibers.

12. The absorbent pad of claim 10 which further comprises an additional layer positioned between the absorbent layer and the backing layer which additional layer is comprised of thermoplastic fibers.

13. The absorbent pad of claim 11 wherein the bicomponent fibers are comprised of a polyester core surrounded by a sheath of polyethylene.

14. The absorbent pad of claim 10 wherein the absorbent layer is further comprised of pulp fluff.

15. The absorbent pad of claim 10 wherein the cover layer has fibers with a denier from about 1.0 to about 4.0.

16. The absorbent pad of claim 10 wherein the absorbent layer has fibers with a denier from about 1.0 to about 4.0.

* * * * *